United States Patent
Rothschild

(10) Patent No.: US 9,535,019 B1
(45) Date of Patent: Jan. 3, 2017

(54) LATERALLY-OFFSET DETECTORS FOR LONG-RANGE X-RAY BACKSCATTER IMAGING

(71) Applicant: American Science and Engineering, Inc., Billerica, MA (US)

(72) Inventor: Peter J. Rothschild, Newton, MA (US)

(73) Assignee: American Science and Engineering, Inc., Billerica, MA (US)

(*) Notice: Subject to any disclaimer, the term of this patent is extended or adjusted under 35 U.S.C. 154(b) by 170 days.

(21) Appl. No.: 14/499,572

(22) Filed: Sep. 29, 2014

Related U.S. Application Data

(60) Provisional application No. 61/886,742, filed on Oct. 4, 2013.

(51) Int. Cl.
  *G01N 23/201* (2006.01)
  *G01N 23/203* (2006.01)
  *G01V 5/00* (2006.01)

(52) U.S. Cl.
  CPC ............ *G01N 23/203* (2013.01); *G01V 5/0025* (2013.01)

(58) Field of Classification Search
  CPC .... G01V 5/0025; G01N 23/203; G01N 23/04; G01N 2223/053
  See application file for complete search history.

(56) References Cited

U.S. PATENT DOCUMENTS

| | | | |
|---|---|---|---|
| 6,424,695 B1 | 7/2002 | Grodzins et al. | 378/87 |
| 7,505,562 B2 | 3/2009 | Dinca et al. | 378/87 |
| 7,551,715 B2 | 6/2009 | Rothschild et al. | 378/57 |
| 2006/0245548 A1* | 11/2006 | Callerame | G01N 23/203 378/160 |

OTHER PUBLICATIONS

Jaffe, "Underwater Optical Imaging: the Design of Optimal Systems," *Oceanography—Review & Comment*, pp. 40-41 (Nov. 1988).

* cited by examiner

*Primary Examiner* — Hoon Song
(74) *Attorney, Agent, or Firm* — Sunstein Kann Murphy Timbers LLP

(57) ABSTRACT

A method for imaging a target with an x-ray scatter apparatus. Air scatter from air intervening between the x-ray scatter apparatus and a target overwhelms x-ray scatter from the target in that x-ray scatter from a position on the target is no more than 10% of the x-ray scatter due to intervening air scatter that reaches at least one point in the detector plane of the x-ray scatter apparatus. The target is illuminated with a beam of x-rays scanned across the target, and x-rays scattered by the target are detected using a detector with a centroid displaced with respect to the beam axis by at least five feet. The detector signal is then processed to generate an image of the target. The beam of x-rays may be unshielded, and/or the detector may be uncollimated.

3 Claims, 6 Drawing Sheets

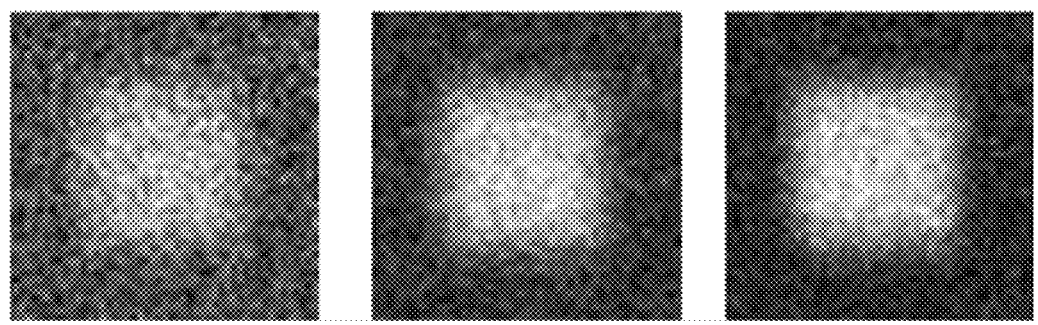
8" Offset  5' Offset  10' Offset
*FIG. 7A*  *FIG. 7B*  *FIG. 7C*

LATERALLY-OFFSET DETECTORS FOR LONG-RANGE X-RAY BACKSCATTER IMAGING

The present application claims priority from U.S. Provisional Application Ser. No. 61/886,742, filed Oct. 4, 2013, and incorporated herein by reference.

TECHNICAL FIELD

The present application relates to the field of x-ray backscatter imaging, and, more particularly, to imaging at significant stand-off distances.

BACKGROUND OF THE INVENTION

A common imaging modality, in many parts of the electromagnetic spectrum, entails illuminating an object with an illuminating beam and then detecting radiation that is scattered by the object. Flash photography is an example. Over the course of the last 20 years, x-ray backscatter imaging, for example, has become a well-established means of carrying out one-sided x-ray inspection of vehicles, cargo containers, baggage, and personnel. Because organic contraband such as drugs and explosives is characterized by a relatively low atomic number, it is effective at scattering x-rays and these materials therefore show up as bright, easily visible regions in a backscatter image.

Target discrimination and the enhancement of target return signal over foreground scatter noise has long been a challenging issue in active remote sensing modalities such as radar or lidar. Local scatter rejection is particularly vexing in the domain of x-ray scatter in that polarization-selecting strategies that are employed in radar and lidar to enhance target return relative to foreground scatter are unavailing in x-ray scatter applications where the Compton scattering mechanism from bound electrons is polarization non-preserving.

Jaffe, *Underwater Optical Imaging: The Design of Optimal Systems*, Oceanography, pp. 40-41 (November, 1988) discusses a common instance of imaging through a scattering medium, namely underwater photography. In that context, scatter avoidance by lateral offset of the illuminating beam and the camera is believed to be effective only at distances up to 2-3 attenuation lengths, i.e., where the scatter return by the imaged object itself is attenuated by the intervening water by no more than about $e^3 \approx 20$. In x-ray backscatter applications, not only can x-ray attenuation at lower energies be substantially greater, but, additionally, at all energies, the cross section for scatter by atoms of the intervening air is comparable to that of the distant target itself, since atoms of substantially comparable atomic numbers are involved.

Time-gating has been suggested for discrimination of distant x-ray targets, as in U.S. Pat. No. 7,505,562 (Dinca), incorporated herein by reference, where time-resolution capabilities are deemed of particular advantage in long-range applications that are noise-limited by air scatter. Time-gating, however, might be rendered impractical due to temporal constraints of source and/or detector response.

The use of the differential étendue (the product of detector area times the solid angle a detector subtends relative to a source) presented by offset backscatter detectors has been suggested "in order to optimize the efficiency of a system in discriminating among x-rays scatter from various selected regions of the space penetrated by a probe beam," in U.S. Pat. No. 6,424,695 (Grodzins, the "'695 patent), incorporated herein by reference.

FIG. 1, reproduced from the '695 patent, shows laterally offset detectors in the context of x-ray backscatter imaging. A beam 10 of penetrating radiation is incident upon one or more objects 12 and 20 which may be concealed from view, such as by surface 30 which may be the surface of a wall or may be a surface of an enclosure or container 14. A volume 2 posterior to surface 30 or contained within enclosure 14 may be referred to, herein, without limitation, simply as "enclosure 14." "Penetrating radiation" refers to electromagnetic radiation of an appropriate range of energy and intensity as to penetrate container 14 and objects 12 and 20, and will be referred to, without limitation, in the following description as x-ray radiation. Beam 10 will similarly be referred to, without limitation, as an x-ray beam. Beam 10 is generated by a source (not shown) of penetrating radiation which may, for example, be an x-ray tube or a radioactive source. Plane 30 tangential to a point at which beam 10 penetrates surface enclosure 14 is referred to as the "plane of incidence."

X-rays 10 are scattered by objects 12 and 20, giving rise, for example, to scattered x-ray paths 16, 18, 22, 24, and 26. Backscatter detectors 3, 4, 5, and 6 are disposed on the same side of container 14 as source 46, with detectors 3 and 5 on one side of beam 10 and detectors 4 and 6 on the opposite side of the beam. X-rays 10 are preferably in the form of a pencil beam that is raster scanned in the plane perpendicular to the line of the detectors The Grodzins '695 patent taught that the position and relative sizes of backscatter detectors 3, 4, 5, and 6 may be chosen to optimize the efficiency of the system in discriminating among x-rays scattered from various selected regions of the space penetrated by beam 10, and to obtain images that enhance scattering features located at different depths into container 14. Radiation scattered from more distant scattering sources such as object 20 is detected preferentially by exterior detectors 5 and 6 relative to interior detectors 3 and 4 since the detected flux is substantially proportional to the solid angles (depicted in projection in the plane of the paper) designated respectively as $\Omega_6^{far}$ and $\Omega_3^{far}$, subtended by the respective detectors. The collection area of exterior detectors 5 and 6 may be increased relative to the collection area of the interior detectors 3 and 4 in order to enhance the magnitude of $\Omega_6^{far}$ relative to $\Omega_3^{far}$ for the more distant scattering sources 20. By way of contrast, for nearer object 12, the ratio of solid angles (depicted in projection in the plane of the paper) designated respectively as $\Omega_6^{near}$ and $\Omega_3^{near}$, subtended by exterior detectors 5 and 6 relative to interior detectors 3 and 4, favors detection by the interior detectors. The Grodzins '695 patent nowhere suggests that discrimination between a more distant scattering source and a less distant scattering source might apply to intervening air scatter.

U.S. Pat. No. 7,551,715 (Rothschild, the "'715 patent"), incorporated herein by reference, teaches "separating the location of the x-ray detectors from the x-ray source." In the case of the '715 patent, it is taught that the detectors are closer to the scattering object than the rest of the imaging system, allowing for more flux scattered by the target and less flux scattered by intervening air to be collected than if the detectors were co-located with the x-ray source and other equipment. However, the '715 patent teaches that, in order to discriminate the return signal from a target relative to air scatter, detectors are to be placed at a distance from the source in the direction toward the target. This is described in col. 14, lines 34ff of the '715 patent, referring to the configuration of detectors shown in FIG. 2 (FIG. 23 of the '715 patent).

Referring to FIG. 2, which appears in the '715 patent as FIG. 23, detectors 140 near to the primary beam 200 receive an air scatter signal which will 'fog' the image. The noise caused by this effect is mitigated, according to the '715 patent, by reading the signals from detectors 140 at different distances in separate channels 74, so that person 76 is imaged in only one detector, and that image contains only the air scatter background from that detector (or the set of detectors in that region). Detectors 140 located along the path of the primary beam 200 that are not near to the target receive much less signal from the target and therefore have a much higher ratio of noise to signal than detectors located near to the target. The overall signal-to-noise ratio may be improved by ignoring the entire signal from detector which are not near the target.

However, operationally, it may be desirable to use detectors which are remote from the target, and which are located at substantially the same distance from a target as the source 46 of the primary beam. No solution to this problem has ever been suggested.

SUMMARY OF EMBODIMENTS OF THE INVENTION

In accordance with embodiments of the present invention, a method is provided for imaging a target with an x-ray scatter apparatus, where the scatter per unit area reaching the x-ray scatter apparatus from a position on the target is no more than 10% of the x-ray scatter due to intervening air scatter that reaches at least one point in the detector plane of the x-ray scatter apparatus due to intervening air scatter. The method has steps of:
  illuminating the target with a beam of x-rays scanned across the target, the beam characterized by a beam axis;
  detecting x-rays scattered by the target using a detector characterized by a centroid displaced with respect to the beam axis by at least five feet, thereby generating a detector signal; and
  processing the detector signal to generate an image of the target.
In accordance with further embodiments of the invention, the beam of x-rays may be unshielded, and/or the detector may be uncollimated.

BRIEF DESCRIPTION OF THE FIGURES

The foregoing features of the invention will be more readily understood by reference to the following detailed description, taken with reference to the accompanying figures, in which:

FIG. 7A-7C show simulated images of a plastic target at 100 ft. for detector center offsets relative to the probe beam of 8", 5 ft., and 10 ft., respectively.

DETAILED DESCRIPTION OF EMBODIMENTS OF THE INVENTION

Definitions

Figure 1:
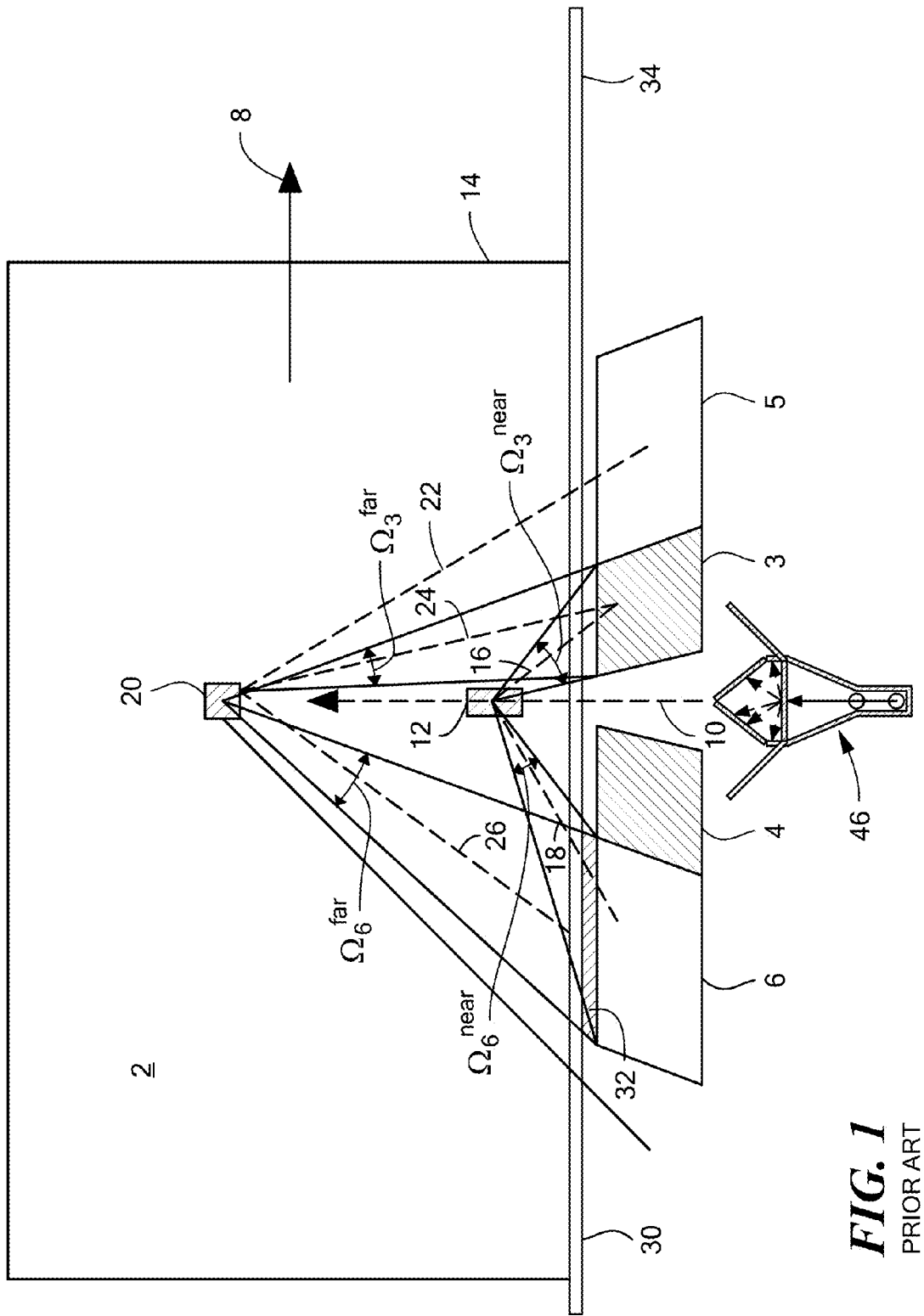
FIG. 1 schematically depicts x-ray backscatter imaging as taught in the prior art, using detectors which are laterally offset relative to an illuminating beam.
Figure 2:
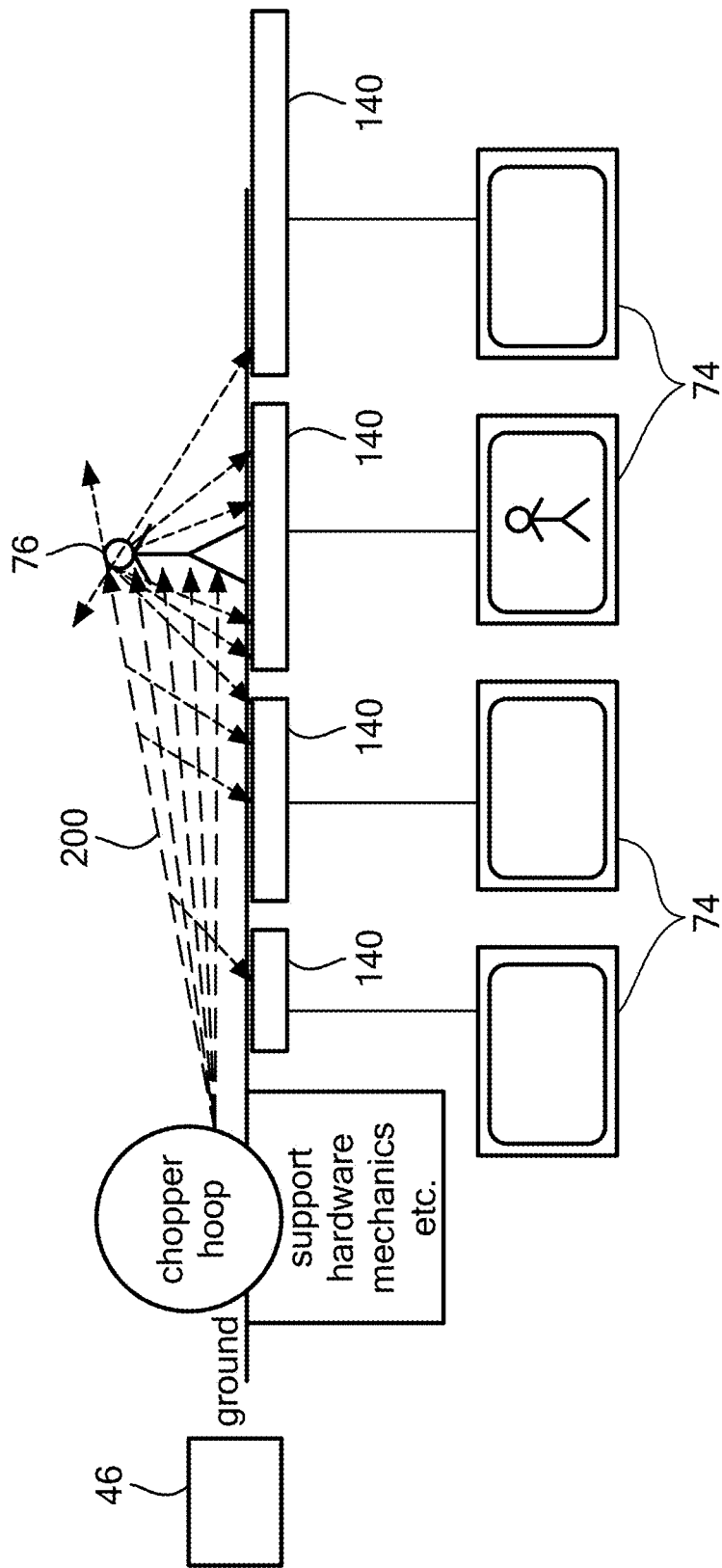
FIG. 2 schematically depicts a solution to x-ray air scatter as taught in the prior art, using detectors disposed at distinct distances along a line of sight from a source of an x-ray primary beam and an object under inspection.

In the present description, and in any appended claims, the term "source beam" or, equivalently, "probe beam," shall refer to a beam of electromagnetic radiation, typically x-rays, scanned across a target for purposes of imaging that target on the basis of detected backscatter radiation.

The term "distant," as used herein to characterize the position of an object relative to an imaging system, shall refer to the position of the object, of any size, for which the scatter of a source beam that is subtended at the position of origin of the source beam is much smaller than the scatter due to an intervening medium. For purposes of this definition, "much smaller" shall mean at least one order of magnitude smaller.

Distance (designated by numeral 29 in FIG. 3) between an imaging system and a target is defined herein as the shortest distance as measured along the probe beam axis from a transverse plane intersecting one or more backscatter detectors and a transverse plane intersecting the target.

The plane (designated by numeral 261 in FIG. 3) which is transverse to the beam axis and intersects at least one backscatter detector and which is the closest such plane to the target shall be referred to herein as the "detector plane."

It is clear from the foregoing definitions, that the distance, as measured in physical units, which corresponds to the threshold of "distant," as defined above, is a function of the energy spectrum of the source beam.

The term "beam plane" shall refer to a plane instantaneously containing a propagation direction of the probe beam and perpendicular to a displacement between the probe beam and a center of at least one backscatter detector.

The term "center of a detector" is defined to mean a geometrical centroid of a volume of detecting material used for deriving a detector signal from incident scattered penetrating radiation.

The term "lateral offset," unless otherwise dictated by context, shall mean the distance between the axis of a probe beam and the centroid of the backscatter detector that is closest to the probe beam axis measured along a perpendicular to the beam axis.

The term "image" shall refer to any multidimensional representation, whether in tangible or otherwise perceptible form, or otherwise, whereby a value of some characteristic is associated with each of a plurality of locations (or, vectors in a Euclidean space, typically $\mathcal{R}^2$) corresponding to dimensional coordinates of an object in physical space, though not necessarily mapped one-to-one thereonto. An image may comprise an array of numbers in a computer memory or holographic medium. Similarly, "imaging" refers to the rendering of a stated physical characteristic in terms of one or more images.

The term "unshielded," as applied to the probe beam, indicates that there is no appreciable shielding of the propagation path of the probe beam to preclude scatter emission into the field of view of the backscatter detectors.

The term "uncollimated," as applied to a detector, shall mean that there is no substantial collimation of the field of view of said detector.

The term "overwhelming air scatter," as used herein and in any appended claims, shall refer to air scatter which gives rise to a flux of photons in the detector plane, as defined above, which exceeds the flux of photons in the same plane arising due to scatter by a specified distant target.

Figure 3:
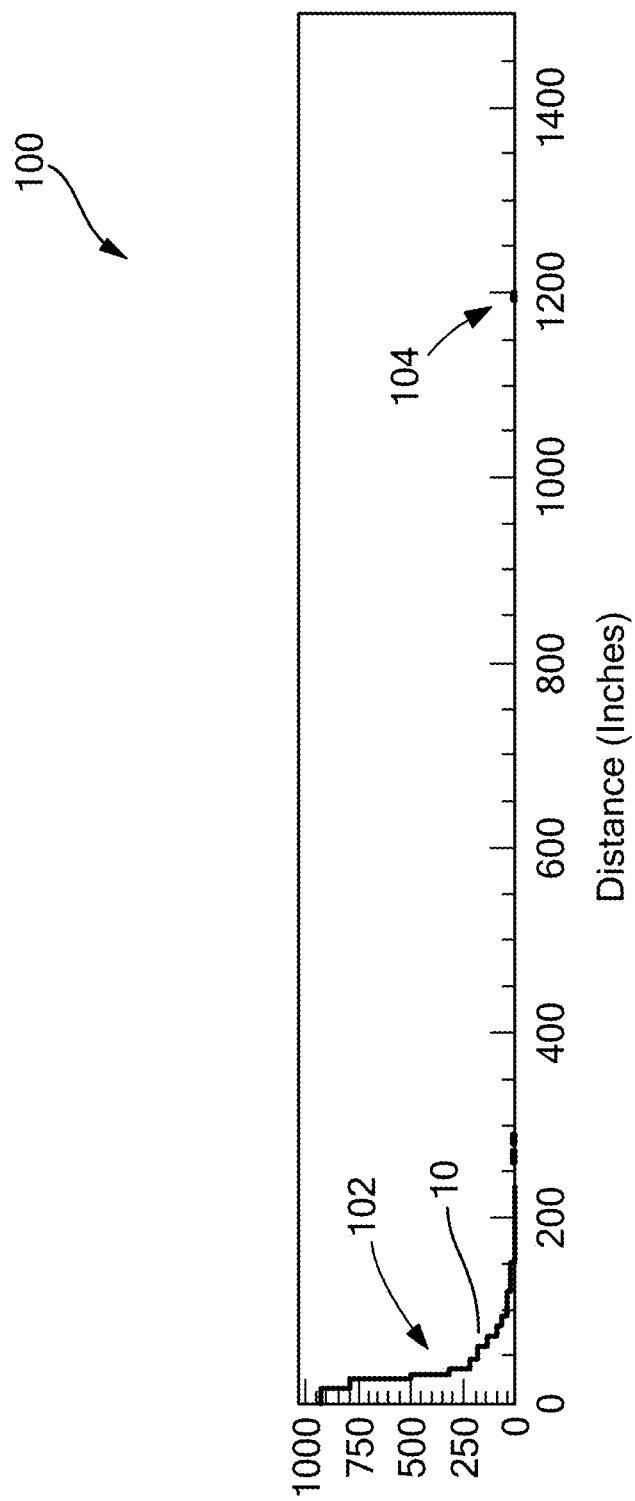
FIG. 3 shows a plot of simulated scatter detection as a function of the distance of the point of first scatter from a beam directed toward a plastic target at 100 ft.
Figure 4:
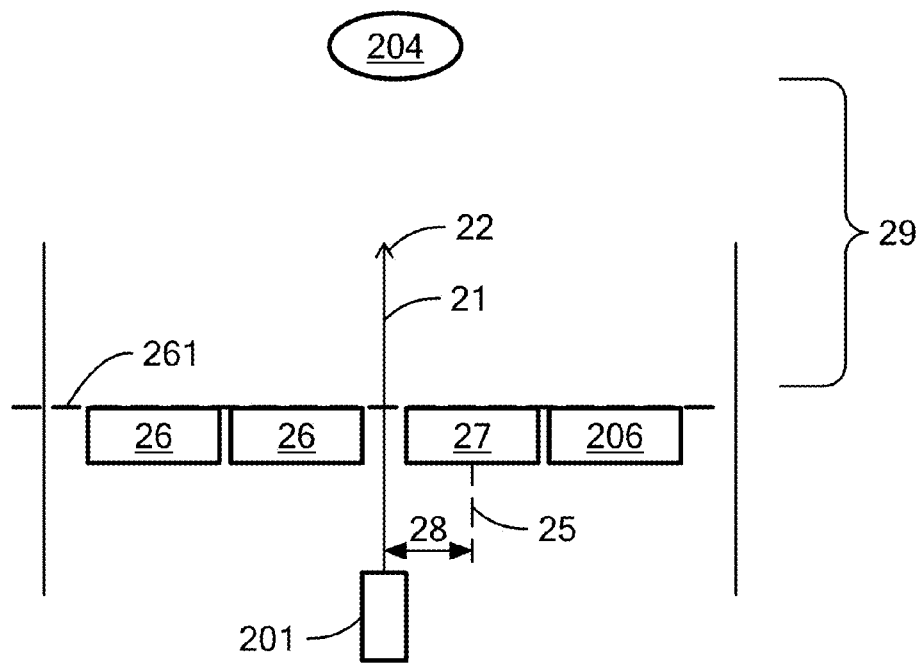
FIG. 4 shows a configuration of backscatter detectors about a probe beam.

The '695 patent discussed above addressed baggage and cargo inspection applications. However, some imaging applications call for a much larger separation between the imaging system (containing the source and the detectors) and the object being imaged than is common in baggage or cargo inspection systems. For example, some security applications where Vehicle-Borne IEDs (VBIEDs) need to be detected are most efficaciously detected at stand-off distances as large as 50-100 feet between the system and the suspicious vehicle. For these applications, computer simulations show that the dominant source of x-rays entering the backscatter detectors is near-field air scatter. Indeed, at least one point in the detector plane, air scatter exceeds any x-rays scattered by the target by at least a factor of 10. In FIG. 4, the closest backscatter detector 27 to beam axis 21 is positioned such that its center 25 is displaced by a lateral distance 28 of only 8 inches from the beam plane (the plane, directed into the page, and containing beam axis 21), with all pertinent terms as defined below). FIG. 3 depicts a plot 100 of detected photons, in arbitrary units, as a function of the distance of the point of first scatter from the detector plane (as defined below) assuming a plastic target at a distance of 100 feet, intervening air at ground-level STP, and a distribution of incident energy characterizing an x-ray beam with an endpoint energy of 225 keV. As is apparent from the plot of FIG. 3, photon detection events 102 due to scatter by the nearby intervening medium far outweigh photon detection events 104 due to scatter by the distant target.

Reference may be made to the '715 patent for the rudiments of backscatter imaging, and for nomenclature employed herein, to the extent usage is consistent with the foregoing definitions. Thus, referring to FIG. 4, probe beam 21 propagates along a probe beam axis (also designated by numeral 21) from source 201 (typically including an x-ray tube and collimator) in the direction indicated by arrow 22 toward target 204. Detectors 206 detect x-ray photons scattered by the target 204 as well as x-ray photons scattered by air in the path traversed by beam 21, in response to which detectors 206 generate one or more detector signals represented by curve 100 in FIGS. 6A-6D. Probe beam 21 is unshielded in that no shielding is provided to preclude scatter emission into the field of view of the backscatter detectors. Similarly, none of the detectors shown in FIG. 3 is collimated.

Figure 5:
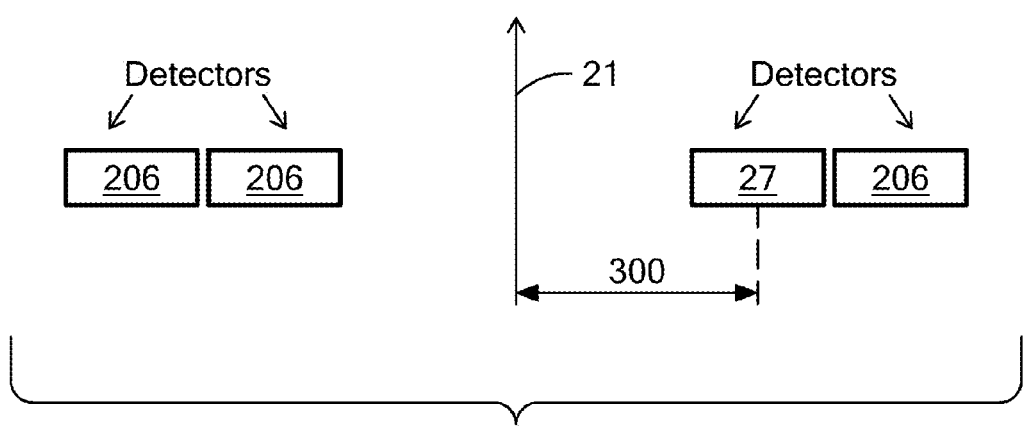
FIG. 5 shows a configuration of backscatter detectors laterally displaced about a probe beam, in accordance with an embodiment of the present invention.
Figure 6A:
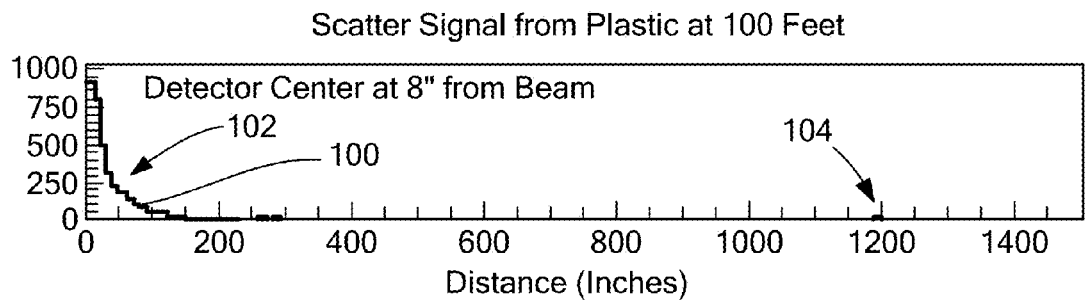
FIGS. 6A-6D show plots of simulated scatter detection as a function of the distance of the point of first scatter from a beam directed toward a plastic target at 100 ft. at detector center offsets relative to the probe beam of 8", 5 ft., 10 ft., and 20 ft., respectively.
Figure 6B:
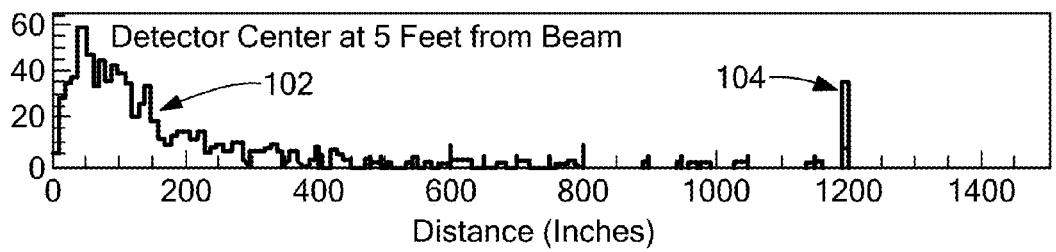
Figure 6C:
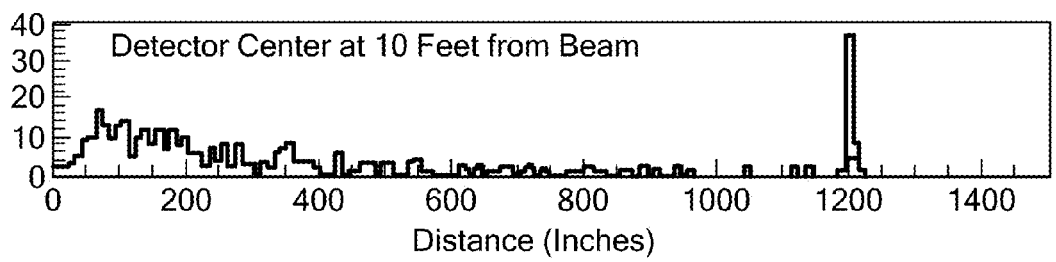
Figure 6D:
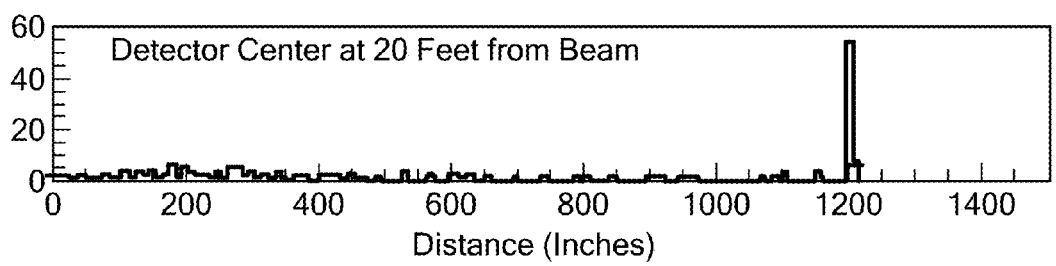

In accordance with embodiments of the present invention, the problem of near-field air scatter is solved, for the first time ever, by laterally moving the backscatter detectors 206, 27 away from the beam axis 21, thereby greatly reducing the contribution 102 of near-field air scatter to the detected signal 100 (shown in FIGS. 6A-6D). In FIGS. 6A-6D, the backscatter signal 100 from the plastic target 204 is shown for a lateral offset of the backscatter detectors 206, 27 from the beam plane of 8", 5', 10', and 20', respectively, indicating, respectively, the contribution 12 from air scatter and the contribution 14 from the target. It can be seen that with increasing lateral offset 300 (shown in FIG. 5), the relative fraction of scatter 104 originating from the distant object increases dramatically, compared with the detected air scatter 102.

Objects made of light elements, e.g. air and plastic, have similar cross sections for higher x-ray energies >~30 keV, where the photoelectric cross section no longer dominates. The interactions differ by the densities, 0.0012 (air) vs. ~1 (plastic); i.e., a difference of 800. Backscatter detection is dominated by the product of the interaction probability times the solid angle from the target to the backscatter detector. If the backscatter detectors are close to the x-ray source, the solid angle for capturing the scatter from the first few meters of air, dominates the density factor of 800. But if the backscatter detectors are laterally displaced, the solid angle for detecting the air scatter drops rapidly, while the signal from the target decreases only moderately.

The improvement in the signal-to-noise ratio (SNR) as a function of the lateral offset distance 300 of the detectors 206, 27 from beam axis 21 can be calculated by taking the ratio of the detected scatter signal from the distant object to the fluctuation in the air scatter signal. Since x-ray backscatter is a Poisson process, the fluctuation in the air scatter background is simply the square root of the air scatter signal (the mean value of the air scatter being simply subtracted). The calculated SNR values for the different lateral detector offsets are shown in Table 1. The energy distribution of the x-ray beam used in order to derive the air scatter background is that of bremsstrahlung emission from an x-ray target impinged upon by 225 keV electrons, with no filtration of the backscatter return.

TABLE 1

| Lateral Offset | Signal | Air Scatter Background | SNR |
| --- | --- | --- | --- |
| 8 Inches | 36 ± 6 | 3841 ± 62 | 0.6 |
| 5 Feet | 36 ± 6 | 789 ± 28 | 1.3 |
| 10 Feet | 36 ± 6 | 350 ± 19 | 2.0 |
| 20 Feet | 36 ± 6 | 150 ± 12 | 3.0 |

The effect of the lateral detector offset can also be clearly seen using computer-generated backscatter images, as shown in FIGS. 7A-7C. FIGS. 7A-7C shows simulated images of a five-inch cube of water positioned 30 feet in front of a backscatter detector, for lateral detector offsets of 8", 5', and 10', respectively. Even at a distance of only 30 feet, the improvement in the image quality is clearly evident as the detector offset is increased. A detector offset of at least 5 feet is preferred.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A method for imaging a target, with an x-ray scatter apparatus, in the face of overwhelming air scatter, the x-ray scatter apparatus characterized by a detector plane, the method comprising:

a. illuminating the target with a beam of x-rays scanned across the target, the beam characterized by a beam axis;

b. detecting x-rays scattered by the target, the x-rays characterized by a scatter per unit area, using a detector characterized by a centroid displaced with respect to the beam axis by at least five feet, thereby generating a detector signal, wherein where the scatter per unit area reaching at least one point in the detector plane of the x-ray scatter apparatus from a position on the target is no more than 10% of x-ray scatter reaching the x-ray scatter apparatus due to intervening air scatter; and c. processing the detector signal to generate an image of the target.

2. A method according to claim 1, wherein the beam of x-rays is unshielded.

3. A method according to claim 1, wherein the detector is uncollimated.

* * * * *